(12) United States Patent
Anitua Aldecoa (10) Patent No.: US 8,123,524 B2
(45) Date of Patent: Feb. 28, 2012

(54) DENTAL IMPLANT, PIECES TO BE CONNECTED TO A DENTAL IMPLANT, AND THE INTERNAL CONNECTION BETWEEN THE DENTAL IMPLANT AND EACH PIECE

(75) Inventor: Eduardo Anitua Aldecoa, Vitoria (ES)

(73) Assignee: Biotechnology Institute, I Mas D, S.L., Vitoria (ES)

( * ) Notice: Subject to any disclaimer, the term of this patent is extended or adjusted under 35 U.S.C. 154(b) by 143 days.

(21) Appl. No.: 11/911,374

(22) PCT Filed: Apr. 6, 2006

(86) PCT No.: PCT/IB2006/001008
§ 371 (c)(1), (2), (4) Date: Jun. 20, 2008

(87) PCT Pub. No.: WO2006/109176
PCT Pub. Date: Oct. 19, 2006

(65) Prior Publication Data
US 2008/0299516 A1 Dec. 4, 2008

(30) Foreign Application Priority Data

Apr. 12, 2005 (ES) .................................. 200500864

(51) Int. Cl.
*A61C 8/00* (2006.01)
(52) U.S. Cl. ...................................................... 433/173
(58) Field of Classification Search .................. 433/173, 433/174
See application file for complete search history.

(56) References Cited

U.S. PATENT DOCUMENTS

| 2,083,092 A | 1/1936 | Richer |
| 3,125,910 A | 3/1964 | Kavalar |
| 3,584,667 A | 6/1971 | Reiland |
| 4,581,957 A | 4/1986 | Dossier |
| 4,900,381 A | 2/1990 | Guenther et al. |
| 4,960,381 A | 10/1990 | Niznick |
| 5,030,095 A | 7/1991 | Niznick |
| 5,076,788 A | 12/1991 | Niznick |
| 5,122,059 A | 6/1992 | Duerr et al. |
| 5,137,407 A | 8/1992 | Yamamoto |
| 5,171,117 A | 12/1992 | Seidl |
| 5,195,892 A | 3/1993 | Gersberg |
| 5,207,132 A | 5/1993 | Goss et al. |
| 5,279,190 A | 1/1994 | Goss et al. |
| 5,334,024 A | 8/1994 | Niznick |
| 5,350,302 A | 9/1994 | Marlin |

(Continued)

FOREIGN PATENT DOCUMENTS

CA 2286224 A1 11/1998
(Continued)

*Primary Examiner* — Cris L Rodriguez
*Assistant Examiner* — Eric Rosen
(74) *Attorney, Agent, or Firm* — Browdy and Neimark, PLLC (57) ABSTRACT

Dental implant and piece to be connected to a dental implant are provided. Both the implant and the piece are capable of being connected to each other by an internal connection to the dental implant. The internal connection principally comprises an anti-rotational part and a cylindrical part, with the anti-rotational part being formed by the repetition of a series of anti-rotational components, each of them formed by a series of arcs tangent to each other. This design of the anti-rotational part enables better performance to be obtained than with known anti-rotational designs.

22 Claims, 4 Drawing Sheets

U.S. PATENT DOCUMENTS

| | | | |
|---|---|---|---|
| 5,388,486 A | 2/1995 | Ruzicka et al. | |
| 5,433,606 A | 7/1995 | Niznick et al. | |
| 5,437,551 A | 8/1995 | Chalifoux | |
| 5,549,475 A | 8/1996 | Duerr et al. | |
| 5,782,918 A | 7/1998 | Klardie et al. | |
| 5,810,589 A | 9/1998 | Michnick et al. | |
| 5,823,776 A | 10/1998 | Duerr et al. | |
| 6,053,733 A | 4/2000 | Aspichueta et al. | |
| 6,120,292 A | 9/2000 | Buser et al. | |
| 6,158,310 A | 12/2000 | Goss et al. | |
| 6,168,436 B1 | 1/2001 | O'Brien | |
| 6,227,859 B1 | 5/2001 | Sutter | |
| 6,238,133 B1 | 5/2001 | DeRoche et al. | |
| 6,244,867 B1 | 6/2001 | Aravena et al. | |
| 6,250,922 B1 | 6/2001 | Bassett et al. | |
| D446,859 S | 8/2001 | Hurson | |
| 6,315,563 B1 | 11/2001 | Sager | |
| 6,368,108 B1 | 4/2002 | Locante et al. | |
| 6,375,465 B1 | 4/2002 | Engman et al. | |
| 6,394,806 B1 | 5/2002 | Kumar | |
| 6,416,245 B1 | 7/2002 | Matt | |
| 6,419,489 B1 | 7/2002 | Jorneus et al. | |
| 6,431,866 B2 | 8/2002 | Hurson | |
| 6,537,070 B1 | 3/2003 | Stucki-McCormick | |
| 6,601,486 B2 | 8/2003 | Hansson et al. | |
| 6,623,202 B2 | 9/2003 | Hansson et al. | |
| 6,626,911 B1 * | 9/2003 | Engman et al. | 606/916 |
| 6,632,057 B1 | 10/2003 | Fauchet | |
| 6,644,969 B2 | 11/2003 | Kumar | |
| 6,659,770 B2 | 12/2003 | Crudo | |
| 6,685,412 B2 | 2/2004 | Altarac et al. | |
| 6,702,508 B2 | 3/2004 | Simons et al. | |
| 6,709,270 B2 | 3/2004 | Honkura et al. | |
| 6,726,480 B1 | 4/2004 | Sutter | |
| 6,733,291 B1 | 5/2004 | Hurson | |
| 6,866,508 B2 | 3/2005 | Aldecoa | |
| 7,014,464 B2 | 3/2006 | Niznick | |
| 7,104,797 B2 * | 9/2006 | Rassoli | 433/173 |
| 7,108,510 B2 | 9/2006 | Niznick | |
| 7,112,063 B2 | 9/2006 | Bulard et al. | |
| 7,198,488 B2 | 4/2007 | Lang et al. | |
| 7,249,949 B2 | 7/2007 | Carter | |
| D556,907 S | 12/2007 | Rassoli | |
| 2001/0034008 A1 | 10/2001 | Porter et al. | |
| 2002/0177105 A1 | 11/2002 | Engman | |
| 2003/0068599 A1 | 4/2003 | Balfour et al. | |
| 2003/0113690 A1 | 6/2003 | Hollander et al. | |
| 2003/0120279 A1 | 6/2003 | Hansson | |
| 2004/0093030 A1 | 5/2004 | Cox et al. | |
| 2004/0101808 A1 | 5/2004 | Porter et al. | |
| 2004/0175674 A1 | 9/2004 | Hurson | |
| 2004/0185417 A1 | 9/2004 | Rassoli | |
| 2005/0014108 A1 | 1/2005 | Wohrle et al. | |
| 2005/0136380 A1 | 6/2005 | Niznick | |
| 2005/0186537 A1 | 8/2005 | Gersberg | |
| 2005/0287497 A1 * | 12/2005 | Carter | 433/173 |
| 2007/0037123 A1 | 2/2007 | Mansueto et al. | |
| 2007/0105068 A1 | 5/2007 | Stucki-McCormick | |
| 2007/0117066 A1 | 5/2007 | Jorneus et al. | |

FOREIGN PATENT DOCUMENTS

| | | |
|---|---|---|
| CN | 1062078 A | 6/1992 |
| CN | 1110909 A | 11/1995 |
| CN | 2246495 Y | 2/1997 |
| CN | 1196670 A | 10/1998 |
| CN | 2332376 Y | 8/1999 |
| CN | 1254267 A | 5/2000 |
| CN | 1298288 A | 6/2001 |
| CN | 1428132 | 7/2003 |
| DE | 103 29 207 A1 | 1/2005 |
| EP | 1 021 996 A1 | 7/2000 |
| EP | 1 203 567 A2 | 5/2002 |
| JP | 05-000145 A | 1/1993 |
| JP | 05-118313 A | 5/1993 |
| JP | 07-136198 A | 5/1995 |
| JP | 2001500768 T | 1/2001 |
| JP | 2003518980 T | 6/2003 |
| JP | 3481257 B2 | 10/2003 |
| JP | 2004113718 A | 4/2004 |
| WO | 9952464 A1 | 10/1999 |
| WO | 0027300 A1 | 5/2000 |
| WO | 0149199 A2 | 7/2001 |
| WO | 03020154 A1 | 3/2003 |
| WO | 2004073541 A2 | 9/2004 |
| WO | WO 2004-073541 A | 9/2004 |
| WO | 2005000146 | 1/2005 |
| WO | 2005067811 A1 | 7/2005 |
| WO | 2006012273 A | 2/2006 |
| WO | WO 2006/012273 A | 2/2006 |
| WO | 2006084922 A1 | 8/2006 |
| WO | 2006109176 A1 | 10/2006 |

* cited by examiner

DENTAL IMPLANT, PIECES TO BE CONNECTED TO A DENTAL IMPLANT, AND THE INTERNAL CONNECTION BETWEEN THE DENTAL IMPLANT AND EACH PIECE

TECHNICAL FIELD

The present invention relates to the connection between a dental implant and a prosthetic/prosthodontic element or, in general, any part or piece to be connected to a dental implant, where said connection is of the type known as an "internal connection", as it is made inside the implant.

PRIOR ART

A dental implant is basically a surgical piece with certain biological properties that is inserted into the maxillary bone of a patient and to which is connected a prosthetic element, wherein said prosthetic element is a piece that supports one or more artificial dental pieces. The insertion procedure of the implant is complex, although this can be summarised by an initial creation of an alveolus in the patient's maxillary, a subsequent insertion of the implant, the optional wait involving a specific time for the osseointegration of the implant in the maxillary bone to occur, and the final fitting of the prosthetic element by means of its connection to the dental implant and the subsequent connection of a screw that connects the prosthetic element with the dental implant.

In relation to this last step, the prior art contains multiple types of designs of connections between implants and prosthetic elements, wherein a "connection" is understood as the design of the parts of the implant and the prosthetic element that must be assembled and connected to each other. Generally speaking, the connection between an implant and a prosthetic element must meet diverse requirements, the principal one being that said connection presents a substantially indefinite duration, i.e. that the robustness of the connection is not reduced during the use of the prosthetic element or tooth throughout the life of the patient. This requirement is translated into other more specific ones such as that the distribution of forces or loads to which the prosthetic element is subjected has to be as uniform as possible all the way along the implant so that it does not arise that one part of the implant is especially overloaded leading to the possible deterioration of the connection between the implant and the maxillary bone, due to alterations in the homeostasis or to a physiological replacement of the peri-implant bone tissue or the bone tissue that surrounds the implant (a normal biological process during the life of the patient). Maintenance of an osseointegrated implant during an entire lifetime is conditioned by mechanical factors dependent upon the stresses and load that the implant experiences and which it may transmit to the bone tissue impacting on the calcification or stability of said tissue.

An implant must also be capable of being connected to another type of piece such as the transporter (a piece that is used to transport or transfer the dental implant to the mouth of the patient and to insert and thread the dental implant in the patient's maxillary bone) or other types of prosthodontic elements. These connections must meet their own requirements. An example of these requirements, as far as the connection between the implant and the transporter is concerned, concerns the capability of transmitting the maximum rotation torque between transporter and implant (it should be borne in mind that the transporter allows the implant to be threaded into the patient's bone, as a consequence of which there must be as high a transmission of rotation torque in the connection between transporter and implant in order to facilitate the threading of the implant without causing the plastic deformation of the implant).

There are two different types of connection between a dental implant and a prosthetic/prosthodontic element or, in general, any piece to be connected to an implant: external connections and internal connections. External connections are those in which the assembly zone between the implant and the piece is situated outside the implant, i.e. the implant presents a male character and the piece a female character. In contrast, in internal connections, the connection zone is situated inside the implant, as a consequence of which the implant can be considered the female piece and the piece to be connected to the implant can be considered the male piece.

It has been demonstrated how the internal connections present certain advantages in relation to the external connections, such as, in the case of a connection between implant and prosthetic element, minimising the possibilities of a loosening between the prosthetic element and the implant, and enabling an improved distribution of stresses and a greater stability of the implant/prosthetic element unit in the event of overloading. Furthermore, as an implant with an internal connection can present a head with a smaller height than an implant with an external connection, the former is more suitable for applications in which the implant is inserted in the maxillary bone of the patient in a submersed way, in which, during osseointegration, the implant is hidden beneath the gum. Additionally, an internal connection facilitates the insertion of the prosthetic element, as it is easier to position and fit a male element in a female element than to conduct the opposite process.

The prior art contains multitude types of designs of internal connections between dental implants and prosthetic/prosthodontic elements or, in general, any piece to be connected to a dental implant. The present invention is an alternative to said designs.

BRIEF DESCRIPTION OF THE INVENTION

It is an object of this invention to provide a dental implant and a prosthetic/prosthodontic element or, in general, any piece to be connected to a dental implant, wherein the implant and the piece are capable of being connected to each other by an internal connection, i.e. by a connection in which the piece behaves as a male element and the dental implant behaves as a female element. The inventive internal connection guarantees great strength and at the same time does not compromise the manufacturability or the cost of the dental implant and the piece to be connected to the dental implant.

The internal connection between the implant and the piece principally comprises an anti-rotational part and a cylindrical part. The anti-rotational part must complete a series of functions and requirements. Firstly, its main function is to prevent the piece from rotating in relation to the dental implant. Furthermore, in the event that the piece is a prosthetic element, the anti-rotational part must guarantee the resistance of the implant during the insertion phase of the prosthetic element and facilitate the positioning and insertion of the prosthetic element, creating a guide to facilitate the assembly of the prosthetic element on the dental implant. Additionally, in the event that the piece is a transporter, the anti-rotational part must have the capacity to transmit the necessary torque to insert the implant without causing permanent deformation on the implant.

In the inventive internal connection, the anti-rotational part is formed in a geometry based on arcs that are tangent to each other. This geometry of the anti-rotational part meets the aforementioned requirements, as can be seen in the detailed description of the invention. Furthermore, because the anti-rotational part is based on tangent arcs and, therefore, uses only rounded forms, it prevents the accumulation of stresses at specific points of the anti-rotational part and, by extension, at specific points of the implant and the piece connected to the implant.

In addition, the geometry of tangent arcs is such that there are controlled clearances or gaps between the piece and the implant, and the point of contact between the anti-rotational zones of the piece and the implant is created as far away as possible from the centre of the geometry or the longitudinal axis of the implant and the part (where said axis constitutes the axis of rotation of the piece), thereby increasing the transmission of the rotation torque from the piece to the implant in relation to known designs of anti-rotational parts in which the contact occurs at points that are closer to the longitudinal axis of the implant and the piece.

With regard to the specific embodiment of the dental implant provided with the aforementioned connection, said dental implant comprises a blind hole comprising, in addition to a threaded zone for the connection of a screw, an anti-rotational zone and a cylindrical zone to provide the aforementioned anti-rotational and cylindrical parts of the internal connection. Said blind hole presents a conical inlet that facilitates the insertion of the prosthetic element.

In addition, the dental implant preferably presents a neck in cylindrical form finished optionally in a conical threaded zone. The conical threaded zone improves the stability of the implant during the first phase of surgery (the insertion of the implant in the maxillary bone of the patient), as it increases the friction between implant and bone as the implant is introduced into the bone. The area of contact between the implant and the bone is increased in this area by means of a physical/chemical treatment, such as preferably acid etching of said surface. Optionally it is coated with a preparation with osteoinductive and osteoconductive properties (such as the plasma rich in growth factors described in WO0044314A1), by virtue of which the osseointegration of the implant is accelerated and improved.

The dimensions of the dental implant are calculated to offer optimal strength without resulting in an excessively large implant. Said dimensions are detailed in the description of the figures.

The piece to be connected to the inventive dental implant also presents an anti-rotational area and a cylindrical area to provide the aforementioned anti-rotational and cylindrical parts of the internal connection. Both the anti-rotational area and the cylindrical area present a bevelled end to facilitate the insertion of said piece in the blind hole of the dental implant.

BRIEF DESCRIPTION OF THE DRAWINGS

The details of the invention can be seen in the figures attached, which do not aim to restrict the scope of the invention.

DETAILED DESCRIPTION OF THE INVENTION

Figure 1:
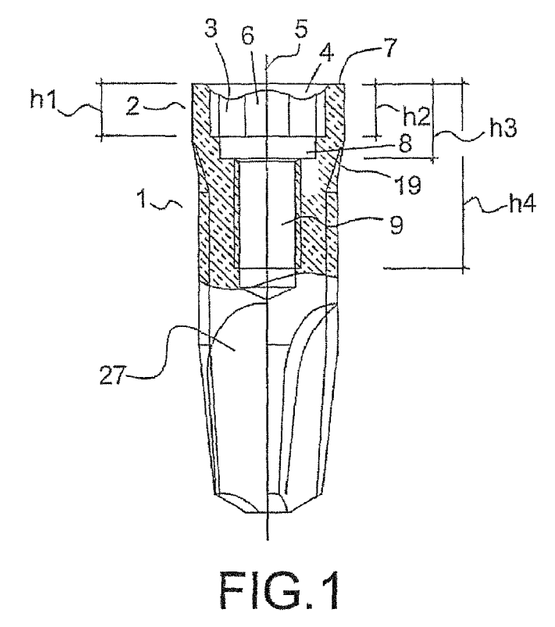
FIG. 1 shows a partially cross-sectioned elevation of an embodiment of a dental implant according to the invention.

FIG. 1 shows a partially cross-sectioned elevation of the preferred embodiment of a dental implant (1) according to the invention. The dental implant (1), like all dental implants, is a piece that is fundamentally lengthened according to a longitudinal axis (5) and finished at the top part by a top surface (7). The main part of the dental implant (1) is a threaded body (27) to be fixed to the maxillary bone of the patient.

In the top part, the dental implant (1) comprises a cylindrical neck (2), with said neck (2) being finished in the area opposite the top surface (7) in a threaded conical area (19), so that the threaded body (27) begins with a conical part in the form of said threaded conical area (19). The neck (2) has a height (h1) of preferably between 0.5 and 2.5 mm.

Furthermore, the dental implant (1) presents a blind hole (3) that constitutes the area of internal connection between the dental implant (1) and the prosthetic/prosthodontic element, i.e., the piece to be connected to the implant. Said blind hole (3) opens from the top surface (7) and comprises a conical inlet (4), an anti-rotational area (6), a cylindrical area (8) and a threaded area (9).

The conical inlet (4) facilitates the introduction of the piece in the blind hole (3) of the dental implant (1). Said conical inlet (3) presents an inclination in relation to the longitudinal axis (5) of preferably between 30° and 60°.

The cylindrical area (8) reinforces the dental implant (1) distributing the lateral loads and guiding the entrance of the piece. The depth (h3) of this cylindrical area (8) must be the maximum that guarantees sufficient material on the wall of the dental implant (1) in order to support the loads to which the dental implant (1) is subjected. For this purpose, the cylindrical area (8) has a depth (h3), measured from the top surface (7) of preferably between 1.3 and 3 mm.

The threaded area (9) provides the area of connection of the screw that links the dental implant (1) to the piece. The diameter of this threaded area (9) must be reduced to guarantee an elevated wall thickness of the dental implant (1) and an elevated strength of the dental implant (1), and at the same time it must be elevated to favour the integrity of the screw in the face of the forces that said screw must withstand. To achieve this, as a compromise solution by means of which these two opposing criteria are met adequately, the invention contemplates threaded area (9) diameters of preferably between 1.1 and 2.5 mm.

The anti-rotational area (6) generally has a depth (h2), measured from the top surface (7) of preferably between 0.7 and 2 mm. By means of these dimensions the anti-rotational area (6) is sufficiently deep for it to present a correct anti-rotational behaviour, but at the same time not sufficiently deep for it to reach the threaded body (27) and have the thickness of the walls of the implant reduced problematically. At the same time, the threaded area (9) preferably has a depth (h4) measured from the top surface (7) of between 3.5 and 7.5 mm. These dimensions ensure a sufficient number of threads in the threaded area (9) to ensure that the connection between the implant and the screw that connects the dental implant and the piece is a suitable connection.

The top surface (7) of the dental implant (1) is totally flat in order to ensure a correct connection with the piece to be connected to the dental implant (1). The size of this top surface (7), delimited by the extent of the blind hole (3) and the diameter of the neck (2) of the dental implant (1), must be sufficiently large to ensure that the connection between the dental implant (1) and the piece can be capable of withstanding the vertical loads without being permanently deformed.

Figure 2:
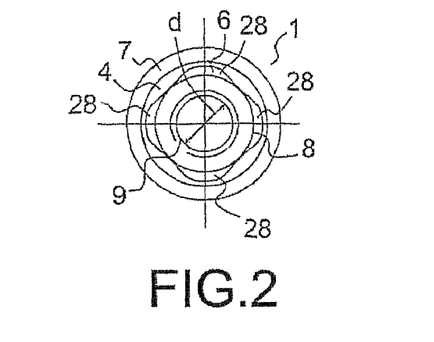
FIG. 2 shows a top view of the dental implant of FIG. 1.

FIG. 2 shows a top view of the dental implant (1), wherein the top surface (7), the conical inlet (4), the anti-rotational area (6) and the cylindrical area (8) can be seen. The anti-rotational area (6) presents in this preferred embodiment a total of four lobules (28). The specific form of the anti-rotational area (6) is detailed in subsequent figures. It can be seen, however, in the figure that the cylindrical area (8) is inscribed in the anti-rotational area (6), with the diameter of the cylindrical area (8) being substantially the same as the smallest diameter (D) of the anti-rotational area (6).

Figure 3:
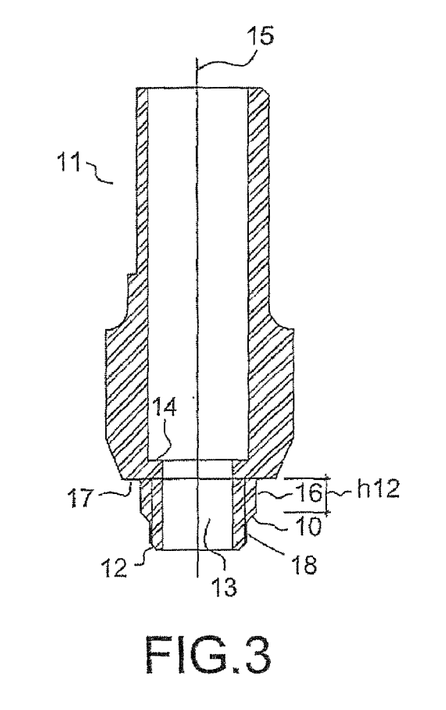
FIG. 3 shows a cross-section elevation of an embodiment of a prosthetic element according to the invention.

FIG. 3 shows a cross-section elevation of an embodiment of a piece (11) to be connected to the inventive dental implant (1), with said piece (11) in this case being a prosthetic element (11). The prosthetic element (11), like the majority of prosthetic elements, is a fundamentally lengthened piece according to a longitudinal shaft (15) and provided with a central through hole (13) in order to insert the screw that connects the prosthetic element (11) to the dental implant (1). Said central through hole (13) includes a support area (14) on which the head of the aforementioned screw rests.

The prosthetic element (11) is provided with a contact surface (17) designed to be supported on the top surface (7) of the dental implant (1). Said contact surface (17) must be perfectly flat to ensure correct closure with the dental implant (1).

From said contact surface (17) projects an anti-rotational area (16), which in turn ends in a bevelled area (10). Said bevelled area (10) softens the contact that occurs between the prosthetic element (11) and the dental implant (1) until the anti-rotational areas (16, 6) of both are correctly oriented during assembly.

Following the bevelled area (10), the prosthetic element (11) includes a cylindrical area (18) that projects from said bevelled area (10) and which ends in a second bevelled area (12). This second bevelled area (12) facilitates the entry of the cylindrical area (18) in the conical inlet (4) of the dental implant (1).

The cylindrical area (18) facilitates the entry of the prosthetic element (11) in the blind hole (3) of the dental implant (1). Thus, in a first phase of introduction it is easy to enter the cylindrical area (18) in the anti-rotational area (6) of the dental implant (1). Additionally, the cylindrical zone (18) absorbs a certain part of the load suffered by the unit formed by the dental implant (1) and the prosthetic element (11) already installed in the mouth of the patient, thereby preventing the load from falling on the anti-rotational area (6) and achieving a more uniform distribution of the stresses on the dental implant (1).

The bevelled area (10) presents an inclination in relation to the longitudinal axis (15) of preferably between 30° and 60°. The anti-rotational area (16) has a depth (h12), measured from the contact surface (17), of preferably between 0.2 and 2 mm. These depths of the anti-rotational area (16) guarantee the operating capacity of said anti-rotational area (16) in the face of lateral loads.

Figure 4:
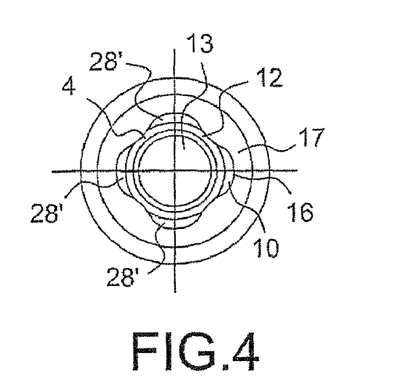
FIG. 4 shows a bottom view of the prosthetic element of FIG. 3.

FIG. 4 shows a bottom view of the inventive prosthetic element (11). The anti-rotational area (16) presents in this embodiment a total of four lobules (28'). The specific form of the anti-rotational area (16) is detailed in the figures below.

Both the anti-rotational area (6) of the dental implant (1) and the anti-rotational area (16) of the prosthetic element (11) are made with a preferably symmetrical outline, i.e., one that presents a certain periodicity or repetition. In the case of the dental implant (1) and the prosthetic element (11) of the figures, the anti-rotational areas (6, 16) consist of the repetition of an anti-rotational component (20, 20') a total of four times, rotated 90° each time until the circumference is completed. Other inventive embodiments with a larger or smaller number of repetitions of the anti-rotational component (20, 20') are contemplated, giving rise to a larger or smaller number of lobules (28, 28').

Figure 5:
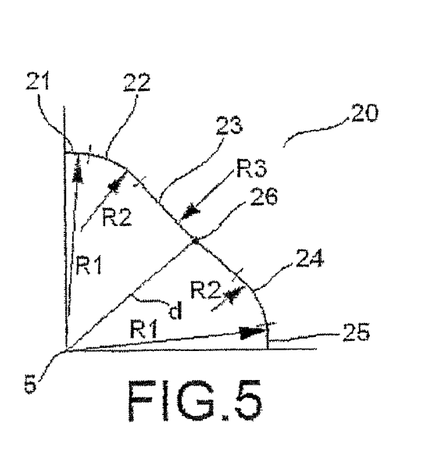
FIG. 5 shows a partial view of an anti-rotational component of the anti-rotational area of the implant of FIG. 1.

FIG. 5 shows the anti-rotational component (20) of the anti-rotational area (6) of the dental implant (1). The anti-rotational component (20) comprises in this case a total of five arcs (21, 22, 23, 24, 25), tangent to each other and determined by respective radii (R1, R2, R3), where the closest point (26) of the anti-rotational component (20) to the longitudinal axis (5) determines the smallest diameter (d) of the anti-rotational component (20) and the anti-rotational area (6). As has been stated, the cylindrical area (8) is inscribed in the anti-rotational area (6) and its diameter preferably coincides with this smallest diameter (d).

In the embodiment of the figure, the centre of the end arcs (21, 25) of the anti-rotational component (20) is situated on the longitudinal axis (5). In addition, the ratio between the radius (R2) of the arcs (22, 24) and the radius (R1) of the end arcs (21, 25) is between 1:2 and 1:3, and the ratio between the radius (R3) of the central arc (23) and the radius (R1) of the end arcs (21, 25) is between 3:1 and 4:1.

Figure 6:
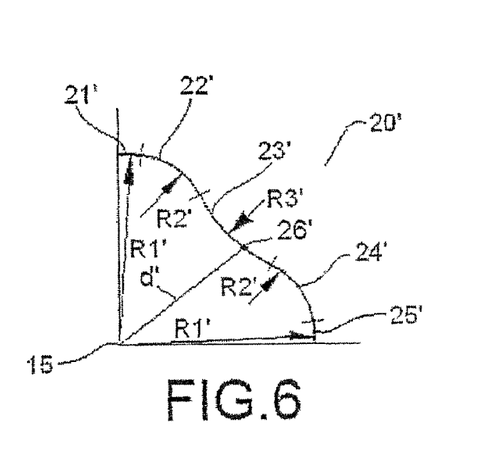
FIG. 6 shows a partial view of an anti-rotational component of the anti-rotational area of the prosthetic element of FIG. 3.

FIG. 6 shows the anti-rotational component (20') of the anti-rotational area (16) of the prosthetic element (11). The anti-rotational component (20') comprises in this case a total of five arcs (21', 22', 23', 24', 25'), tangent to each other and determined by respective radii (R1', R2', R3'), where the closest point (26') of the anti-rotational component (20') to the longitudinal axis (15) determines the smallest diameter (d') of the anti-rotational component (20') and the anti-rotational area (16). The cylindrical area (18) is inscribed in the anti-rotational area (16) and its diameter preferably coincides with this smallest diameter (d').

In the embodiment of the figure, the centre of the end arcs (21', 25') of the anti-rotational component (20') is situated on the longitudinal axis (15). In addition, the ratio between the radius (R2') of the arcs (22', 24') and the radius (R1') of the end arcs (21', 25') is between 1:2 and 1:3, and the ratio between the radius (R3') of the central arc (23') and the radius (R1') of the end arcs (21', 25') is between 1:1 and 1.5:1.

Different embodiments of the anti-rotational components (20, 20') are contemplated with a number of arcs (21, 22, 23, 24, 25, 21', 22', 23', 24', 25') other then five, giving rise to a variable total number of lobules (28, 28').

Figure 7:
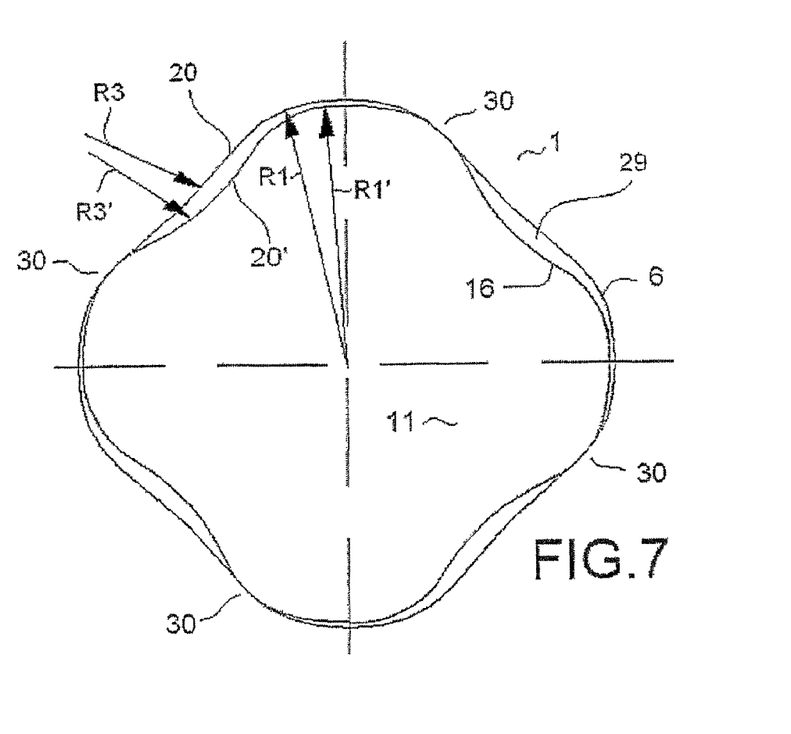
FIG. 7 shows a view of the superimposition or connection of the anti-rotational zones of the dental implant and the prosthetic element of the previous figures.

FIG. 7 shows the anti-rotational part that results from the connection between the anti-rotational area (6) of the dental implant (1) and the anti-rotational area (16) of the piece (11). As can be seen, the different ratio between the radii (R3, R1) of the anti-rotational area (6) and between the radii (R3', R1') of the anti-rotational area (16) enables the appearance of a series of clearances (29), so that the areas of contact (30) between the dental implant (1) and the piece (11) are substantially as distant as possible from the longitudinal axis (5) without the anti-rotational part being prevented from operating as such. In this way the transmission of torque between the piece (11) and the dental implant (1) is increased, being this an interesting effect when the piece (11) is a transporter (1).

The radii (R1, R1') are preferably comprised between 2.5 and 4 mm, dimensions that enable a compromise solution to be reached between the interest in having a high radius (R1, R') to increase the distance from the area of contact (30) to the longitudinal axis (5) and thereby increase the transmission of torque, and the interest in having a reduced radius (R1, R1') so that the top surface (7) is large so that the connection between the implant (1) and the and the prosthetic element (11) can withstand forces or lateral loads.

Figures 8A, 8B:
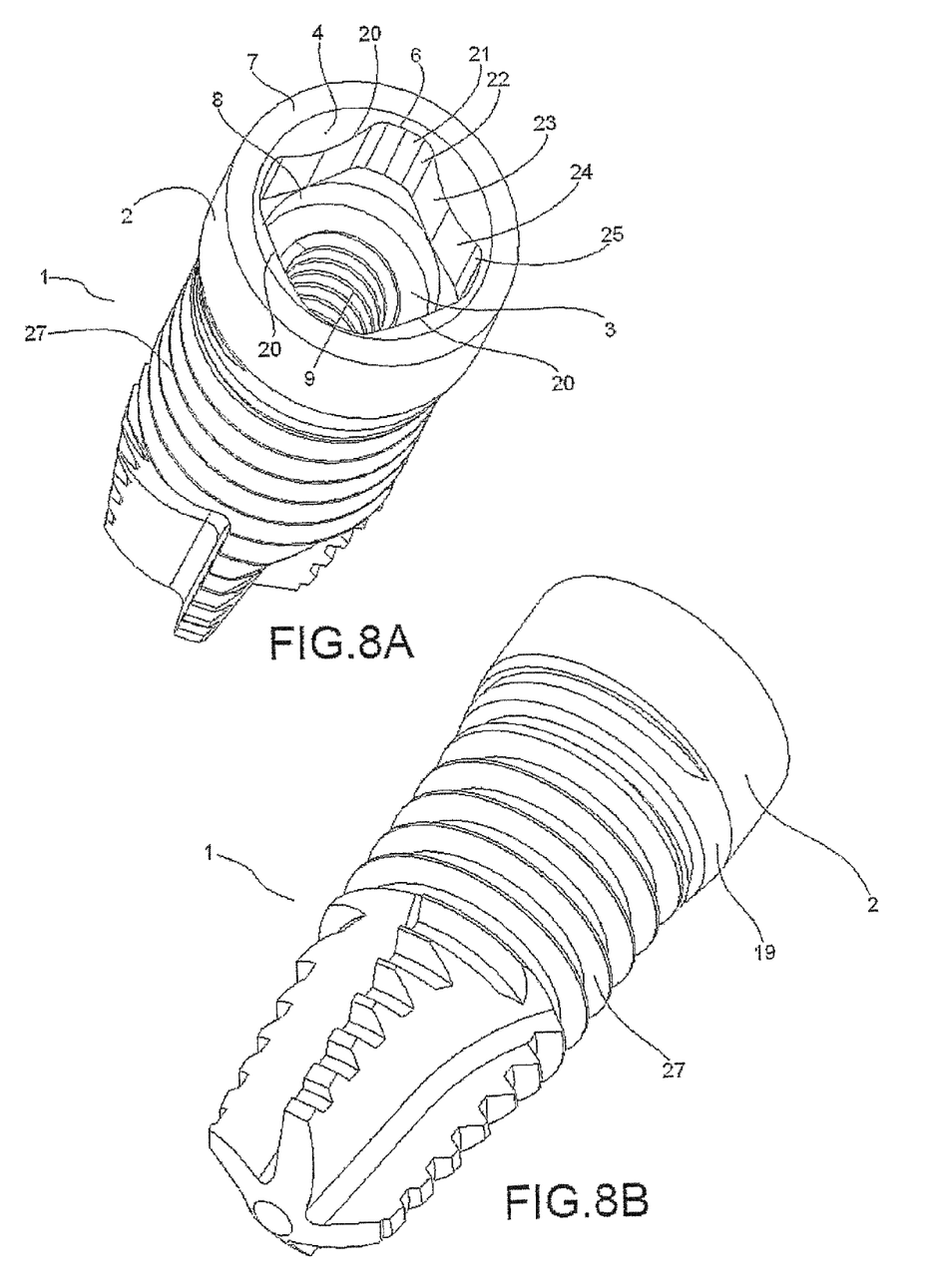
FIGS. 8A and 8B show two perspectives of the dental implant of the previous figures.

FIGS. 8A and 8B show two perspectives of the inventive dental implant (1) detailed in previous figures. FIG. 8A shows a high number of elements detailed in previous figures, with the elements contained in the blind hole (3) that originates from the top surface (7) being particularly appreciable. Thus, it can be seen how said blind hole (3) begins in its uppermost part by the conical inlet (4), and continues with the anti-rotational area (6), the cylindrical area (8) and the threaded area (9). The anti-rotational area (6) consists of four equal anti-rotational components (20), with each one of these anti-rotational components (20) being formed by five arcs (21, 22, 23, 24, 25) tangent to each other. The cylindrical area (8) is inscribed in the anti-rotational area (6). FIG. 8B shows more clearly the exterior of the implant, and details the neck (2), the threaded body (27) inherent to the entire dental implant (1), and the conical threaded area (19) of the inventive implant.

Figure 9:
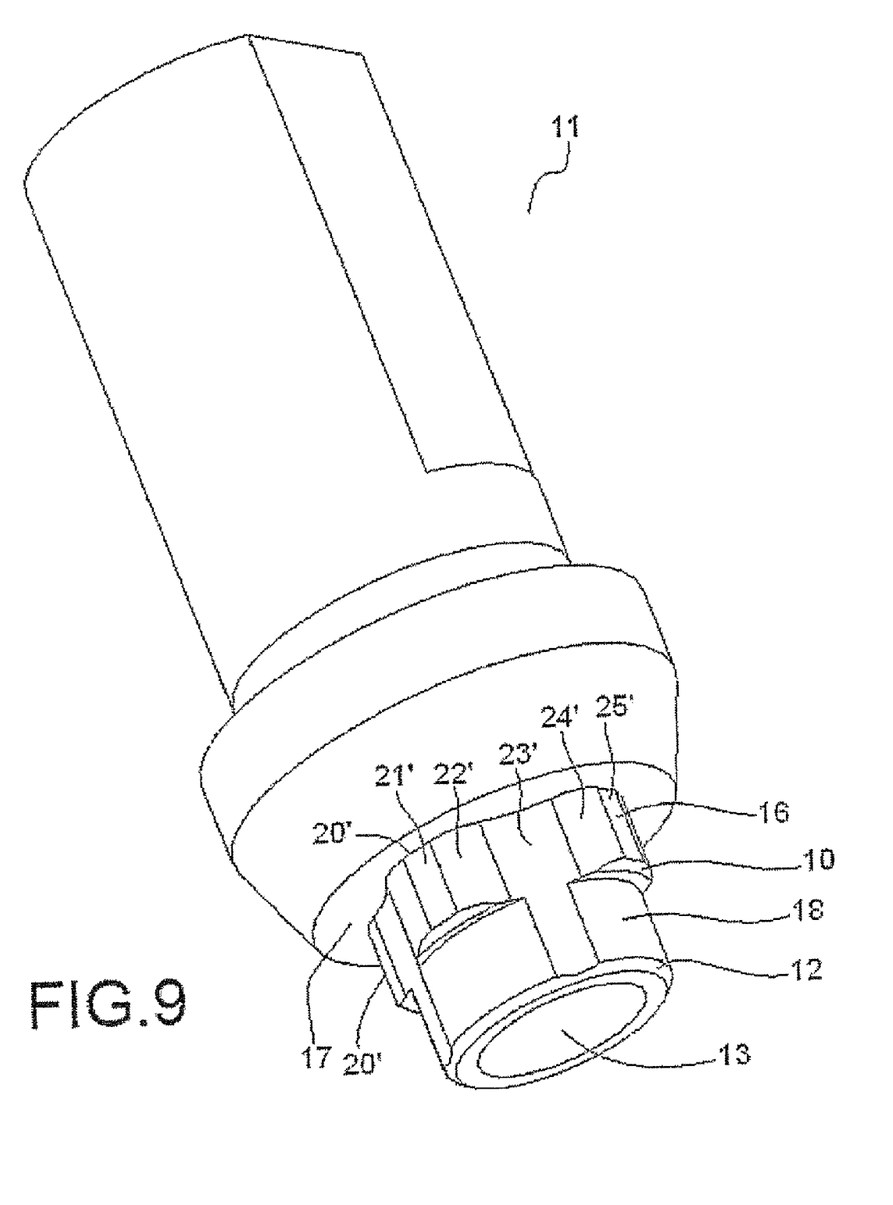
FIG. 9 shows a perspective of the prosthetic element of the previous figures.

FIG. 9 shows a perspective of the inventive prosthetic element (11). This figure shows how, from the contact surface (17), the elements that are to be housed in the blind hole (3) of the dental implant (1) originate: the anti-rotational area (16), finished in a bevel (10), and the cylindrical area (18), finished in a bevelled area (12). It can be seen how the anti-rotational area (16) comprises various anti-rotational components (20'), and that each anti-rotational component (20') is composed of five arcs (21', 22', 23', 24', 25') tangent to each other.

It should be pointed out that the concave part corresponding to the central arc (23') of the anti-rotational component (16) is extended along the entire depth of the cylindrical area (18). This facilitates the fabrication of the piece.

By analysing FIGS. 8A, 8B and 9, an additional advantage of the inventive internal connection can be seen, namely that the cylindrical areas (8, 18) are inscribed in the anti-rotational areas (6, 16), thereby achieving that during the insertion of the prosthetic element (11) into the dental implant (1) a guide is created from the moment at which the cylindrical area (8) of the prosthetic element (11) is introduced into the anti-rotational area (18) of the dental implant (1).

Furthermore, with regard to the piece (11) of FIG. 9, it should be pointed out that the embodiment of pieces (11) not provided with the anti-rotational area (16), but which are compatible with a dental implant (1) that is provided with an anti-rotational area (6), is also contemplated. An example of this type of piece (11) is the transepithelial (a piece that enables the connection of multiple prostheses to one or two dental implants and which for this purpose acts as an adaptor between the dental implant and the prosthetic element bearing multiple dental pieces). These types of pieces (11) must enable the insertion of a bridge bearing multiple dental pieces in the mouth of the patient, respecting the relative position of an implant with respect to another and at the same time facilitating the insertion of the bridge. For this reason, this type of piece comprises only a non-anti-rotational area (18) from the contact surface (17).

The inventive internal connection presents a behaviour that is such that it can be valid for dental implants (1) and pieces (11) of widely valuing sizes. Thus, its application is envisaged in dental implants (1) of a length of between 7 and 35 mm (and even others), threaded body (27) diameters of between 3.3 and 7 mm (and even others), and top surface (7) diameters of between 3.5 and 6.5 mm (and even others). Furthermore, it is envisaged that for a single unit or family of dental implants (1) and pieces (11) made up of implants (1) and pieces (11) of different sizes, the internal connection presented by all of them (1, 11) can be of the same size so as to achieve compatibility between all the dental implants (1) and all the pieces (11).

The invention also contemplates the embodiment of the internal connection in any scale or dimension, on any design of dental implant, and even the application of the internal connection to other types of implants or pieces that are not exclusively dental.

The invention claimed is:

1. Implant (1) and piece (11) unit,
   wherein said unit comprises an implant (1) provided with a first anti-rotational area (6) and disposed along a longitudinal axis (5), and a piece (11) provided with a second anti-rotational area (16),
   wherein the first anti-rotational area (6) cooperates with the second anti-rotational area (16) to prevent the piece (11) from rotating with respect to the implant (1),
   wherein the implant (1) and the piece (11) can be assembled together to form an assembly, with said assembly comprising an area of connection between said first and second anti-rotational areas (6, 16),
   wherein the area of connection comprises clearances (29) between the implant and the piece and areas of contact (30) between the implant and the piece,
   wherein a plane perpendicular to the longitudinal axis of the implant and piece unit extends through both the clearances and the areas of contact,
   wherein said implant is formed along the longitudinal axis (5) and finished on its top part by a top surface (7), and said implant (1) further comprising:
   a blind hole (3) that opens from the top surface (7), wherein said blind hole (3) comprises the first anti-rotational area (6), and a first non anti-rotational area (8) and a threaded area (9),
   wherein the first anti-rotational area (6) comprises a series of first anti-rotational components (20), wherein each first anti-rotational component (20) comprises a series of first arcs (21, 22, 23, 24, 25) tangent to each other and determined by respective radii (R1, R2, R3),
   wherein the closest point (26) of each of the first anti-rotational components (20) to the longitudinal axis (5) determines the smallest diameter (d) of the respective each one of the first anti-rotational components (20) and of the first anti-rotational area (6),
   the first anti-rotational area (6) consists only of four first anti-rotational components (20), the first anti-rotational components (20) being identical and the series of first arcs comprising four first arcs (21, 22, 24, and 25) which are convex with respect to the longitudinal axis (5).

2. Implant (1) and piece (11) unit, in accordance with claim 1, wherein the first non anti-rotational area (8) is formed as a cylindrical area that is inscribed in the first anti-rotational area (6), with the diameter of the cylindrical area (8) being smaller or equal to the smallest diameter (d) of the first anti-rotational area (6).

3. Implant (1) and piece (11) unit, in accordance with claim 2, wherein the blind hole (3) comprises the first anti-rotational area (6) and the first non anti-rotational area (8), and wherein the threaded blind hole (3) comprises a conical inlet (4).

4. Implant (1) and piece (11) unit, in accordance with claim 3, wherein the conical inlet (4) presents an inclination in relation to the longitudinal axis (5) of between 30° and 60°.

5. Implant (1) and piece (11) unit, in accordance with claim 3, wherein the threaded blind hole (3) comprises a threaded area (9) having a depth (h4), measured from the top surface (7), of between 3.5 and 7.5 mm, and presents a diameter of between 1.1 and 2.5 mm.

6. Implant (1) and piece (11) unit, in accordance with claim 2, wherein the first non anti-rotational area (8) has a depth (h3), measured from the top surface (7), of between 1.3 and 3 mm.

7. Implant (1) and piece (11) unit, in accordance with claim 1, wherein the top part of the dental implant (1) comprises a cylindrical neck (2), where the neck (2) has a height (h1) of between 0.5 and 2.5 mm.

8. Implant (1) and piece (11) unit, in accordance with claim 1, wherein the first anti-rotational area (6) has a depth (h2), measured from the top surface (7), of between 0.7 and 2 mm.

9. Implant (1) and piece (11) unit, in accordance with claim 1, wherein, two of the four first arcs which are convex of each of the first anti-rotational components (20) are end arcs (21, 25), a fifth one of the series of first arcs of each of the first anti-rotational components (20) is a central arc (23), and two of the four first arcs which are convex of each of the first anti-rotational components are intermediate arcs (22, 24), wherein one of the intermediate arcs is located between a first of the end arcs and the central arc and a second of the intermediate arcs is located between a second of the end arcs and the central arc.

10. Implant (1) and piece (11) unit, in accordance with claim 9, wherein the end arcs (21, 25) are centered on the longitudinal axis (5).

11. Implant (1) and piece (11) unit, in accordance with claim 10, wherein the ratio between the radius (R2) of the intermediate arcs (22, 24) and the radius (R1) of the end arcs (21, 25) is between 1:2 and 1:3, and the ratio between the radius (R3) of the central arc (23) and the radius (R1) of the end arcs (21, 25) is between 3:1 and 4:1.

12. Implant (1) and piece (11) unit, in accordance with claim 11, wherein the radius (R1) of the end arcs (21, 25) is between 2.5 and 4 mm.

13. Implant (1) and piece (11) unit,
wherein said unit comprises an implant (1) provided with a first anti-rotational area (6) and disposed along a longitudinal axis (5), and a piece (11) provided with a second anti-rotational area (16),
wherein the first anti-rotational area (6) cooperates with the second anti-rotational area (16) to prevent the piece (11) from rotating with respect to the implant (1),
wherein the implant (1) and the piece (11) can be assembled together to form an assembly, with said assembly comprising an area of connection between said first and second anti-rotational areas (6, 16),
wherein the area of connection comprises clearances (29) between the implant and the piece and areas of contact (30) between the implant and the piece, wherein a plane perpendicular to the longitudinal axis of the implant and piece unit extends through both the clearances and the areas of contact,
wherein said piece (11) is formed along the longitudinal axis (15) and provided on its top part with a contact surface (17) to be supported on the top surface (7) of the implant (1), said piece (11) further comprising:
a second non anti-rotational area (18),
the second anti-rotational area (16) comprising a series of second anti-rotational components (20'), wherein each second anti-rotational component (20') comprises a series of second arcs (21', 22', 23', 24', 25') tangent to each other and determined by respective radii (R1', R2', R3'), wherein the closest point (26') of each of the second anti-rotational components (20') to the longitudinal axis (15) determines the smallest diameter (d') of the respective each of the second anti-rotational components (20') and the second anti-rotational area (16),
wherein the second anti-rotational area (16) consists only of four second anti-rotational components (20'), the second anti-rotational components (20') being identical and the series of second arcs comprising four second arcs (21', 22', 24', and 25') which are convex with respect to the longitudinal axis (5).

14. Implant (1) and piece (11) unit, in accordance with claim 13, wherein the second non anti-rotational area (18) is formed as a cylindrical area that is inscribed in the second anti-rotational area (16), with the diameter of the cylindrical area (18) being smaller or equal to the smallest diameter (d') of the second anti-rotational area (16).

15. Implant (1) and piece (11) unit, in accordance with claim 14, wherein the second non anti-rotational area (18) ends in a beveled area (12).

16. Implant (1) and piece (11) unit, in accordance with claim 13, wherein the second anti-rotational area (16) ends in a beveled area (10).

17. Implant (1) and piece (11) unit, in accordance with claim 16, wherein the bevelled area (10) presents an inclination with respect to the longitudinal axis (15) of between 30° and 60°.

18. Implant (1) and piece (11) unit, in accordance with claim 13, wherein the second non anti-rotational area (18) has a depth (h12), measured from the contact surface (17), of between 0.2 and 2 mm.

19. Implant (1) and piece (11) unit, in accordance with claim 13, wherein two of the four second arcs which are convex of each of the second anti-rotational components (20') are end arcs (21', 25'), a fifth one of the series of second arcs of each of the second anti-rotational components (20') is a central arc (23'), and two of the four second arcs which are convex of each of the second anti-rotational components are intermediate arcs (22', 24'), wherein one of the intermediate arcs is located between a first of the end arcs and the central arc and a second of the intermediate arcs is located between a second of the end arcs and the central arc.

20. Implant (1) and piece (11) unit, in accordance with claim 19, wherein the end arcs (21', 25') are centered on the longitudinal axis (5).

21. Implant (1) and piece (11) unit, in accordance with claim 20, wherein the ratio between the radius (R2') of intermediate arcs (22', 24') and the radius (R1') of the end arcs (21', 25') is between 1:2 and 1:3, and the ratio between the radius (R3') of the central arc (23') and the radius (R1') of the end arcs (21', 25') is between 1:1 and 1.5:1.

22. Implant (1) and piece (11) unit, in accordance with claim 21, wherein the radius (R1') of the end arcs (21', 25') is between 2.5 and 4 mm.

* * * * *